United States Patent [19]
Heinz et al.

[11] Patent Number: 4,742,715
[45] Date of Patent: May 10, 1988

[54] APPARATUS FOR THE MANIPULATION OF PROBES

[75] Inventors: Winfried Heinz, Schortens; Wilhelm Schwarz, Kreuztal, both of Fed. Rep. of Germany

[73] Assignee: Fried. Krupp Gesellschaft mit beschränkter Haftung, Essen, Fed. Rep. of Germany

[21] Appl. No.: 932,150

[22] Filed: Nov. 18, 1986

[30] Foreign Application Priority Data

Nov. 19, 1985 [DE] Fed. Rep. of Germany ....... 3540946

[51] Int. Cl.$^4$ .......................... G01N 1/00; C21B 7/24
[52] U.S. Cl. .............................. 73/864.31; 73/DIG. 9
[58] Field of Search .......... 73/864.24, 864.25, 864.31, 73/864.21, DIG. 9, 866.5; 324/447; 374/140; 136/234; 266/99

[56] References Cited

U.S. PATENT DOCUMENTS

| | | | |
|---|---|---|---|
| 3,614,434 | 10/1971 | Horwitz et al. | 73/864.24 |
| 3,902,371 | 9/1975 | Hooper et al. | 73/864.24 |
| 4,228,831 | 10/1980 | Kerns | 73/864.25 |
| 4,258,571 | 3/1981 | Jürgens et al. | 73/864.31 |
| 4,325,909 | 4/1982 | Coulter et al. | 73/864.24 |

FOREIGN PATENT DOCUMENTS 3044609 11/1980 Fed. Rep. of Germany.
2410263 6/1979 France.

OTHER PUBLICATIONS 199-804, de 01.81 "Sublance-System" of Fried. Krupp GmbH, Krupp Industrie- und Stahlbau/Kranbau Wilhelmshaven.
199-806, de 01.81 "Sublance-System, Magazine/-Manipulator" of Fried. Krupp GmbH, Krupp Industrie- und Stahlbau/Kranbau, Wilhelmshaven.

Primary Examiner—Stewart J. Levy
Assistant Examiner—Robert R. Raevis
Attorney, Agent, or Firm—Spencer & Frank

[57] ABSTRACT

Apparatus for manipulating a probe which is to be coupled to a vertically movable probe lance, the lance having a longitudinal axis which is vertically oriented, which apparatus includes a supporting frame supported for pivotable movement about a stationary frame axis between a plurality of operating positions, an openable centering funnel supported by the frame, a lifting carriage supported by the frame for vertical movement relative to the frame, a probe holding clamp supported by the carriage at a location below the funnel, a probe separation device supported by the frame at a location below the probe holding clamp and pivotable relative to the frame about a separation device axis parallel to the frame axis, and a sample holding clamp supported by the frame at a location below the separation device, and in which the funnel is mounted to be vertically movable relative to the frame, and the apparatus further includes a support device connected between the sample holding clamp and the frame and supporting the sample holding clamp for pivotal movement relative to the frame about a sample holding clamp axis parallel to the frame axis.

5 Claims, 2 Drawing Sheets

APPARATUS FOR THE MANIPULATION OF PROBES

BACKGROUND OF THE INVENTION

This invention relates to an apparatus for the manipulation of probes, particularly measuring and sampling probes, that can be coupled to a vertically adjustable probe lance, which apparatus includes a supporting frame that is pivotable into any one of several operating positions about a stationary frame axis parallel to the lance axis. The frame is composed of, going from top to bottom, a centering funnel which is capable of being unfolded, or opened, a lifting carriage vertically slidable on the supporting frame, a probe holding clamp attached to the carriage, a separation device and a sample holding clamp. The separation device is pivotable between the two holding clamps about a pivot axis parallel to the frame axis.

A manipulation apparatus of the type described above, which constitutes a manipulator that permits monitoring of a smelt contained in a metallurgical vessel by means of measuring probes and sampling probes for the measurement of temperatures/bath status or for sampling, is described in FRG-OS No. 30 44 609 A1. In addition to the probe lance serving as a transport arrangement, a magazine and, under certain circumstances, a receiving device such as a discharge funnel, are associated with the manipulation apparatus. The receiving device receives the sampling head disconnected from the sampling probe and directs it to a laboratory room for testing.

The stored probes can be removed individually from the magazine, which is composed of magazine sections arranged next to each other longitudinally, and can be carried to a receiving position parallel to the lance axis. In the latter position, they can be taken over by the manipulation apparatus by operating the centering funnel, which functions simultaneously as a centering clamp, and the probe holding clamp, at least when the apparatus assumes the magazine position adapted to the receiving position. The manipulation apparatus can then be pivoted to a measuring position in which the axis of the firmly clamped probe coincides at least substantially with the lance axis.

To couple the probe, the probe lance seized and guided by the centering funnel is immobilized on the way down to the probe as soon as it has travelled about two thirds of the required coupling distance. Subsequently to that, the coupling procedure is completed as the probe is moved toward the probe lance by the raising of the lifting carriage with the probe holding clamp attached thereto. Before raising the probe, the centering funnel, which is not vertically adjustable with respect to the supporting frame, must be unfolded.

The coupling movement sequences described are time-consuming and demanding with respect to control technology: a short coupling time is particularly desirable so that probes can be exchanged as rapidly as possible and the measuring movements required for the monitoring of the metallurgical vessel can be effected in rapid succession.

One further disadvantage of the known manipulation apparatus is that neither the sample holding clamp nor the probe holding clamp is attached pivotably to the supporting frame in a pivoting fashion. During sampling, the supporting frame must therefore effect several pivoting movements after separation of the sampling head first to move the sampling head toward the testing area and then, i.e. after pivoting back to the measuring position, to relieve the remaining probe through discharge into the metallurgical vessel. Several pivoting movements are also required when the remainder of the probe cannot be fed to the metallurgical vessel because of the associated pollution and must instead be removed via an additional down pipe.

SUMMARY OF THE INVENTION

An object of the invention is to provide a manipulation apparatus of the type described above in which the travel movements involved in coupling probes to a probe lance as well as in disconnecting sampling heads from a sampling probe are simplified and can be executed with little loss of time.

The above and other objects are achieved, according to the invention, in an apparatus for manipulating a probe which is to be coupled to a vertically movable probe lance, the lance having a longitudinal axis which is vertically oriented, which apparatus includes a supporting frame, means supporting the frame for pivotable movement about a stationary frame axis between a plurality of operating positions, an openable centering funnel supported by the frame, a lifting carriage supported by the frame for vertical movement relative to the frame, a probe holding clamp supported by the carriage at a location below the funnel, a probe separation device supported by the frame at a location below the probe holding clamp and pivotable relative to the frame about a separation device axis parallel to the frame axis, and a sample holding clamp supported by the frame at a location below the separation device, by the improvement wherein: the funnel is mounted to be vertically movable relative to the frame; and the apparatus further comprises support means connected between the sample holding clamp and the frame and supporting the sample holding clamp for pivotal movement relative to the frame about a sample holding clamp axis parallel to the frame axis.

The underlying idea of the invention is thus embodied in two manipulation devices of the manipulation apparatus, namely the centering funnel operating also as a centering clamp, and the sample holding clamp, with an additional degree of freedom possibility with respect to the supporting frame in that, while the centering funnel is vertically adjustable with respect to the supporting frame, the sample holding clamp can be pivoted about a pivot axis parallel to the frame axis.

Because of the vertical adjustability of the centering funnel with respect to the lifting carriage, the coupling process can be simplified and accelerated in that the probe lance is brought into a preset position remains stationary and the lifting carriage carries out the entire coupling travel after seizing the probe lance by means of the centering funnel which it drags along.

The coupling process is thus composed of the movements of the centering funnel and the lifting carriage up to the centering of the measuring lance with respect to the probe, followed by the unfolding of the centering funnel and the remaining travel of the lifting carriage and of the no-longer effective centering funnel up to the final fixing of the probe to the probe lance; the unfolding of the centering funnel can be triggered in this process after the coupling movement of the centering funnel and of the lifting carriage has been interrupted temporarily.

A particularly fast coupling process can be realized by having the unfolding take place on the run, i.e., without interrupting the coupling movement.

The swingable arrangement of the sample holding clamp makes it possible to remove the sample seized by the latter—independently of movement by the supporting frame—out of the range of the probe lance and of the vessel monitoring aperture located underneath it, and to throw it, for example, into the discard funnel of a down pipe. Immediately after the pivoting away of the sample holding clamp, the remaining sample can be brought to the metallurgical vessel by the opening of the probe holding clamp. Because of the swingability of the sample holding clamp, the remainder of the probe can be brought to a second down pipe without additional movement of the supporting frame; the two down pipes and associated discard funnels are advantageously positioned in the vicinity of the magazine containing the probes.

Adaptation of the movement of the centering funnel to that of the lifting carriage can be achieved by using two parallel-connected drive elements, in particular motor-driven cylinders. In an especially simple embodiment of the invention the centering funnel is attached to the lifting carriage.

The centering funnel is advantageously braced in this case by an extension adapter which is mounted on the top side of the lifting adapter.

If the centering funnel is rigidly anchored to the lifting carriage, the drive for the carriage may consist of one or more motor-driven cylinders or of a gear wheel drive. The lift carriage is preferably moved by means of a hydraulic cylinder whose travel can be interrupted for the unfolding of the centering funnel.

In a particularly advantageous embodiment of the invention, the centering funnel features a switching unit by means of which it is automatically unfoldable as a function of the adjustable length of travel by the lifting carriage. In a simple version, the switching unit may consist of a limit switch that is actuated by the lifting carriage after completion of a preset length of travel and thereby causes the centering funnel to open.

BRIEF DESCRIPTION OF THE DRAWING

The invention is described in greater detail below with reference to the drawing,. wherein.

DESCRIPTION OF THE PREFERRED EMBODIMENTS

Figure 1:
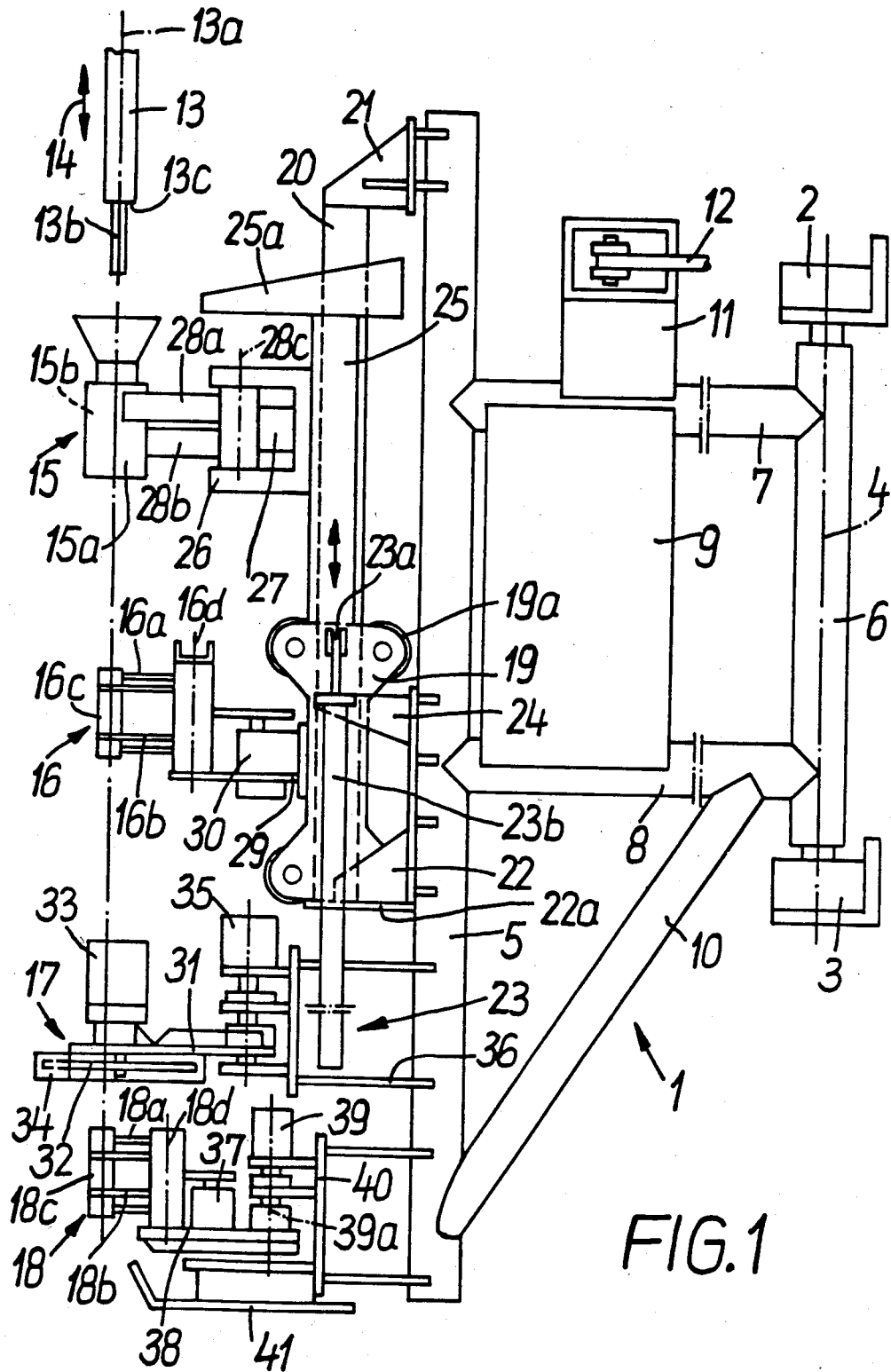
FIG. 1 is showing a simplified side elevational view of a preferred embodiment of the invention

The manipulation apparatus designed as a manipulator is provided with supporting frame 1 which is suspended, so as to pivot about vertical frame axis 4, from two bearing brackets 2 and 3 of a stationary element such as a bearing structure above the metallurgical vessel to be monitored.

Supporting frame 1 has, as support elements, two vertically extending tubes 5 and 6 that are connected to each other by means of two horizontally extending tubes 7 and 8 linked to each other by lateral sheet metal braces 9. Additional stiffening is provided by a diagonal tube 10 which forms a triangle with tubes 5 and 8.

Upper horizontal tube 7 is provided additionally with a connecting bracket 11 to which is linked a piston rod 12 of a hydraulic cylinder assembly. Operation of the latter assembly effects pivoting of the manipulation apparatus between a magazine position outside the range of the monitoring aperture of the metallurgical vessel involved and a measuring position in the range of lance axis 13a of a probe lance 13.

The hydraulic cylinder that moves supporting frame 1 can be replaced by a suitable swinging drive, in particular a hydraulic one.

Probe lance 13, which is vertically moveable in the directions of double arrow 14 by separate apparatus has at its lower end a connection section 13b which permits the loading or removal of a probe (not shown), particularly a measuring or sampling probe. Such a probe lance for handling probes is described in U.S. Pat. No. 4,258,571 and in the brochure 199-804, de 01.81 "Sublance-System" of Fried. Krupp GmbH, Krupp Industrie- und Stahlbau/Kranbau Wilhelmshaven, D-2940 Wilhelmshaven.

To the side of tube 5 directed away from frame axis 4, supporting frame 1 includes going from top to bottom, a number of centering and manipulation elements, namely a centering funnel 15—capable of being unfolded—for centering of probe lance 13 and the probe involved, a probe holding clamp 16, a separation device 17 for the separation of the sampling head of a sampling probe, and a sample holding clamp 18. The centering and holding devices are capable of being opened to a sufficient extent to be out of the region occupied by a probe even when frame 1 is pivoted about axis 4.

Centering funnel 15 and probe holding clamp 16 are adjustable vertically by means of a lifting carriage 19 which is supported on a guide rail 20 by means of upper and lower guide wheels 19a that permit movement of carriage 19 along rail 20. Rail 20 is anchored at its top and bottom to tube 5 by brackets 21 and 22 which are configured to serve at the same time as stops determining the ends of the travel path of lifting carriage 19.

The drive for lifting carriage 19 consists of a hydraulic cylinder 23 having a piston rod 23a hinged to the lifting carriage in the vicinity of upper guide wheels 19a and a cylinder housing 23b anchored to tube 5 by a bracket 24.

At the upper end of lifting carriage 19 is mounted an extension adapter 25 which partially encircles guide rail 20, adapter 25 carrying a protective plate 25a at its upper end. In addition, a housing 26 extends from extension adapter 25 and carries a (schematically shown) drive unit 27 (see FIG. 2 and 3) and pivot arms 28a and 28b which support respective funnel halves 15a and 15b to be pivoted by drive unit 27. Funnel halves 15a and 15b contact one another at a mating plane parallel to the plane of the Figure so that, in the Figure, half 15a is visible and half 15b is hidden. Funnel halves 15a and 15b can be pivoted about axes 28c, supported in housing 26, by actuation of drive unit 27 with the result that centering funnel 15 is folded open or shut, i.e. the funnel halves are moved apart or together. Probe holding clamp 16 consists, as is well known, of two clamp arms 16a and 16b that are equipped with prismatic clamp surfaces 16c and are fixed to be pivotable about a clamp axis 16d, to lifting carriage 19 by means of a bracket plate 29. The rotary drive for the clamp arms consists of a rotary wing motor 30 also mounted to bracket plate 29.

Separation device 17 underneath probe holding clamp 16 features, as essential components, a separation disk 32 held by a pivotable arm 31, disk 32 being driven by a separation disk motor 33, preferably an electric motor, and being partially enclosed by a protective cage 34. Arm 31 is pivotally attached via a pneumatic rotary motor 35 to a bracket 36 of tube 5. By activation of the rotary motor 35, separation disk 32 can be swung close to a probe (whose axis coincides with lance axis 13a shown here) held by the manipulation apparatus, so that the separation process can be initiated.

Sample holding clamp 18, whose clamp arms 18a, 18b equipped with prismatic clamp surfaces 18c can be pivoted about clamp axis 18d by means of a rotary wing motor 37, is also supported by tube 5 via a pivotable arm 38 driven by an associated rotary motor 39 and supported by a bracket 40. By activation of rotary motor 39, sample holding clamp 18 can be swung, independently of the position of supporting frame 1, about vertical rotation axis 39a away from underneath centering and holding elements 15 and 16.

Except for components 18a, 18b and 18c, sample holding clamp 18 is protected from below by a guard plate 41 which is also connected to bracket 40.

Manipulation in accordance with the invention proceeds as follows:

To receive a probe held vertically outside a magazine (cf. FRG-OS No. 30 44 609), supporting frame 1 is swung into the magazine position by operation of hydraulic cylinder piston rod 12, while holding clamps 16 and 18 and centering funnel 15 are open and separation device 17 assumes a rest position outside the area of the above-mentioned centering and manipulation elements. Lifting carriage 19 is in the lower starting position shown, i.e., it is resting on limit stop surface 22a of bracket 22. When the magazine position is reached, motor 30 is activated, whereby clamp arms 16a, 16b are moved toward one another and the probe is clamped tight. In a similar manner, centering funnel 15 is closed by activation of drive unit 27 and, in the process, seizes, with its downwardly directed end section, the upper portion of the probe. This ensures that the latter will, at a later moment, be slipped over and coupled to connection section 13b of probe lance 13.

Thereupon, supporting frame 1 is pivoted to a measuring position in which the probe that has been dragged along lies along the axis of probe lance 13 and underneath the latter. In this process, probe lance 13 assumes a preset coupling position with respect to the manipulation apparatus. The coupling process is initiated, while probe lance 13 remains stationary, by the raising of lifting carriage 19 by means of hydraulic cylinder 23. Centering and manipulation elements 15 and 16 remain closed so that the probe is raised toward probe lance 13 and finally slipped over its connection section 13b. Following the relative centering of measuring lance and probe, centering funnel 15 is opened by activation of drive unit 27, while holding clamp 16 remains closed, before lifting carriage 19 along with probe holding clamp 16 completes the remaining upward travel so that during the remaining upward travel the probe is pressed against lance shoulder 13c. Upon completion of the coupling process effected in this manner, probe holding clamp 16 is opened, lifting carriage 19 is lowered to the lower starting position and supporting frame 1 is swung back into the originally described magazine position.

As soon as the probe has completed the desired measurement (in particular, measurement of temperature and condition of bath) or sampling, the manipulation apparatus is started again.

After the raising of probe lance 13 with the coupled, spent probe to a preset separation position, the supporting frame is again swung back into the measuring position. Then, the spent probe is clamped tight by closing of holding clamps 16 and 18 before separation of the probe is effected by raising probe lance 13. The no-longer usable measuring probe (in the case of temperature or bath condition measurement) can then be dropped into the metallurgical vessel to be monitored by opening of holding clamps 16 and 18.

If a sample was taken by the probe attached to the probe lance, the sampling head to be tested is separated by means of separation device 17 before the unusable probe remainder is discarded. To this effect, separation disk 32 is rotated by separation motor 33 before swinging arm 31 is pivoted by rotary motor 35 into cutting position between holding clamps 16 and 18. This pivot motion results in a probe remainder above separation disk 32 and a sampling head underneath the separation disk. The two separated portions of the sampling probe continue to be held for the time being by probe holding clamp 16 and sample holding clamp 18.

After the pivoting, or, to save time, during the pivoting, of separation device 17 back to its rest position, sample holding clamp 18, with the sampling head tightly clamped into it, is moved by rotary motor 39 away from under the probe remainder so that clamp 16 can be opened to drop the probe remainder into the metallurgical vessel through the monitoring aperture without further pivoting of supporting frame 1.

With the pivoting of supporting frame 1 back into the magazine position, the sampling head comes within the reach of a receiving apparatus, such as a discard funnel with associated down pipe, into which it can be thrown, or dropped, by the opening of sample holding clamp 18, and forwarded to the subsequent test. But the receiving apparatus can also be configured with respect to the manipulation apparatus in such a manner that the sampling head reaches a position permitting its removal merely by the pivoting motion of sample holding clamp 18—i.e., about axis 39a while supporting frame 1 remains in its measuring position.

Depending on space available, the receiving apparatus can also be mounted so that the sampling head is released and forwarded to the receiving apparatus while supporting frame 1 is in an intermediate position—i.e., before completing the pivoting of the supporting frame back into the magazine position.

To save time, the invention can advantageously be combined with two mutually distinct receiving apparatuses, in the form of down pipes, preferably located outside the area of the probe lance in the vicinity of the magazine, i.e., near the magazine position of the manipulation apparatus.

With such an arrangement, the supporting frame of the manipulation apparatus can be moved into the magazine position immediately upon the disconnection of the spent probe—if suitable, together with a rotating separation disk—before either the probe as a unit is, or the sampling head and the probe remainder are, dropped into separate down pipes after action movement by the sample holding clamp.

The advantages achieved by the invention are that the manipulation of probes for the monitoring of a metallurgical vessel can be simplified and performed more rapidly than heretofore.

The use of a centering funnel which is vertically adjustable with respect to the supporting frame makes it possible to carry out the centering and coupling process exclusively by movements of the centering funnel, simultaneously operating as a centering clamp. The use of a sample holding clamp pivotable in relation to the supporting frame makes it possible to move said clamp to a desired position more rapidly and to operate it independently of the supporting frame and its components or in addition to the latter.

The basic structure and function of centering funnel 15, probe holding clamp 16, separation device 17 and holding clamp 18 and disclosed in previously mentioned FRG-OS (laid open German patent application) 3044 609 A1 and in the brochure 199-806, de 01.81 "Sublance-System, Magazine/Manipulator" of Fried. Krupp GmbH, Krupp Industrie- und Stahlbau/Kranbau Wilhelmshaven, D-2940 Wilhelmshaven.

Figure 2:
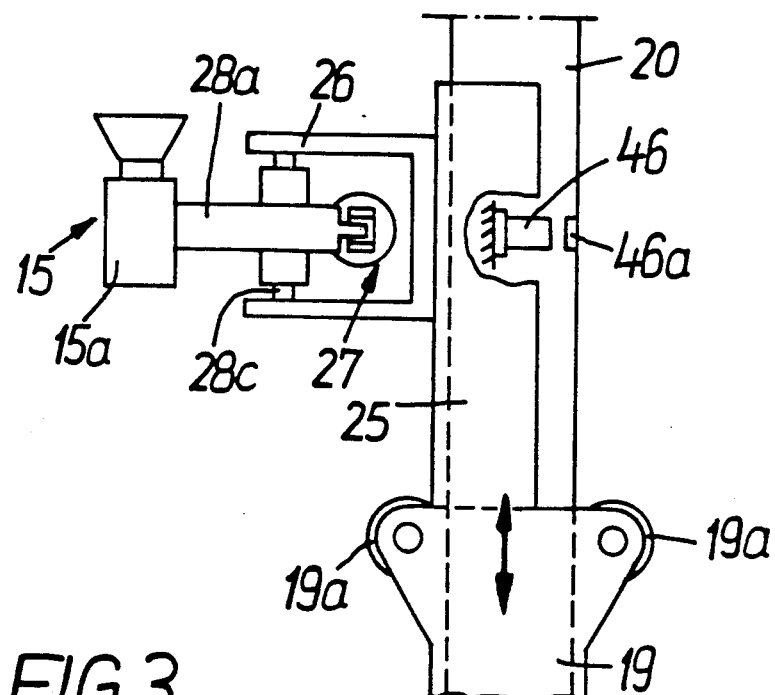
FIG. 2 is a partial side elevational view of the embodiment according to FIG. 1 in the range of the centering funnel.
Figure 3:
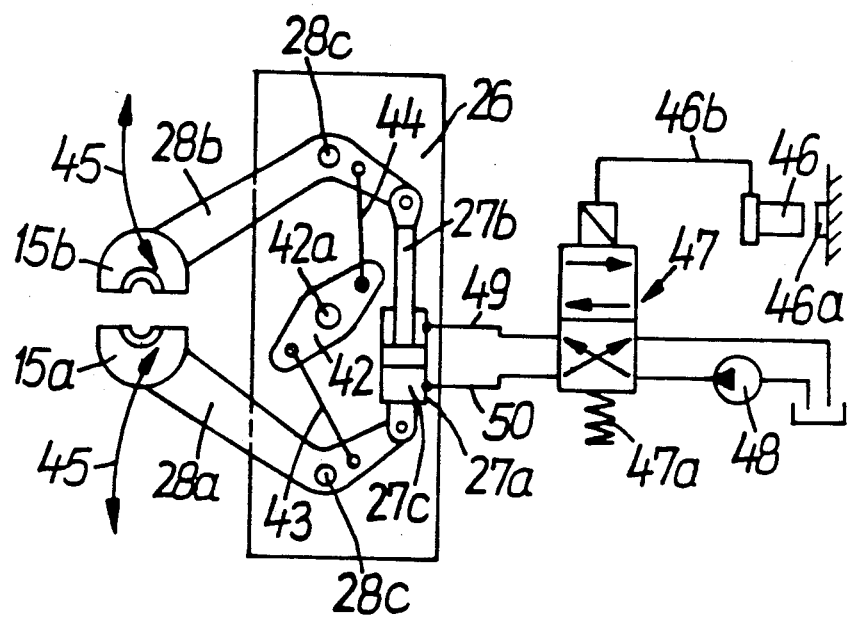
FIG. 3 is a top view of the centering funnel showing schematically also the appertaining control circuit.

The embodiment shown in FIG. 2 and 3 has a drive unit 27 in the form of a hydraulic cylinder, the cylinder 27a and the piston 27b being hinged to pivot arm 28a and 28b respectively (cf. FIG. 3).

Additionally, housing 26 supports a lever 42 pivotable about an axis 42a and connected to pivot arms 28a and 28b via links 43 and 44; by that means, the movement of funnel halves 15a and 15b (shown by arrows 45) relative to housing 26 is made symmetrically.

In the height of centering funnel 15, the extension adapter 25 is equipped with a sensor 46 cooperating with a switching plate 46a, which is fixed to guide rail 20 at a preset position.

Sensor 46 can actuate via line 46b an electromagnetic driven two-way-valve 47, equipped with a spring element 47a. Influenced by this element alone, valve 47 is switched into and held in the shown opening position the centering funnel 15 being folded open. In this position, piston 27b stands under pressure via hydraulic pump 48 and pipe 49, whereas room 27c of cylinder 27a is without pressure.

As long as sensor 46 doesn't face switching plate 46a (as shown in FIG. 2), valve 47 is in the closing position; consequently room 27c is held under pressure via hydraulic pump 48 and pipe 50 and funnel halves 15a and 15b contact one another. As soon as sensor 46 (and correspondently centering funnel 15) approaches to the height of switching plate 46a and therefore reaches a selected position relative to frame 1 (cf. FIG. 1), sensor 46 gives a pulse and thereby switches off valve 47 into the shown opening position.

The present disclosure relates to the subject matter disclosed in German Patent Application, Ser. No. P 35 40 946.0 of Nov. 19th, 1985, the entire specification of which is incorporated herein by reference.

It will be understood that the above description of the present invention is susceptible to various modifications, changes and adaptations, and the same are intended to be comprehended within the meaning and range of equivalents of the appended claims.

What is claimed is:

1. In an apparatus for manipulating a probe which is to be coupled to a vertically movable probe lance, the probe having an upper portion and a lower sample taking head to be inserted into a melt contained in a metallurgical vessel, the lance having a longitudinal axis which is vertically oriented, which apparatus includes a supporting frame, means supporting the frame for pivotable movement about a stationary frame axis between a plurality of operating positions, an openable centering funnel supported by the frame, a lifting carriage supported by the frame for vertical movement relative to the frame, a probe holding clamp supported by the carriage at a location below the funnel, probe separation means, including a probe separation device supported by the frame at a location below the probe holding clamp and pivotable relative to the frame about a separation device axis parallel to the stationary frame axis, for severing the head from the upper portion of the probe and a sample head holding clamp means, supported by the frame at a location below the separation device for clamping the head, the improvement wherein: said funnel is mounted to be vertically movable relative to said frame; and said apparatus further comprises support means connected between said sample head holding clamp means and said frame and supporting said sample head holding clamp means for pivotal movement relative to said frame about a sample head holding clamp axis parallel to the stationary frame axis.

2. Apparatus as defined in claim 1 wherein said funnel is secured to said carriage for vertical movement therewith.

3. Apparatus as defined in claim 2 wherein said carriage comprises an upwardly projecting extension adapter constituting the upper portion of said carriage, and said funnel is secured to said extension adapter.

4. Apparatus as defined in claim 2 wherein said funnel includes switching means responsive to vertical movement of said carriage for automatically opening said funnel when said carriage moves vertically to a selected position relative to said frame.

5. Apparatus as defined in claim 1 for manipulating measuring and sampling probes.

* * * * *